US010589381B2

(12) United States Patent
Peuser et al.

(10) Patent No.: US 10,589,381 B2
(45) Date of Patent: Mar. 17, 2020

(54) METHOD FOR PRODUCING A DENTAL OR MEDICAL INSTRUMENT

(71) Applicant: Gebr. Brasseler GmbH & Co. KG, Lemgo (DE)

(72) Inventors: Christian Peuser, Detmold (DE); Karl-Heinz Danger, Detmold (DE); Michael Kuellmer, Lemgo (DE)

(73) Assignee: GEBR. BRASSELER GMBH & CO. KG, Lemgo (DE)

( * ) Notice: Subject to any disclaimer, the term of this patent is extended or adjusted under 35 U.S.C. 154(b) by 0 days.

(21) Appl. No.: 15/120,903

(22) PCT Filed: Jan. 26, 2015

(86) PCT No.: PCT/EP2015/051505
§ 371 (c)(1),
(2) Date: Aug. 23, 2016

(87) PCT Pub. No.: WO2015/128140
PCT Pub. Date: Sep. 3, 2015

(65) Prior Publication Data
US 2016/0368096 A1 Dec. 22, 2016

(30) Foreign Application Priority Data
Feb. 26, 2014 (DE) .................. 10 2014 203 459

(51) Int. Cl.
*B23K 26/34* (2014.01)
*C23C 24/10* (2006.01)
(Continued)

(52) U.S. Cl.
CPC ................ *B23K 26/34* (2013.01); *A61C 3/02* (2013.01); *B23K 26/0006* (2013.01);
(Continued)

(58) Field of Classification Search
CPC ............ B23K 26/0006; B23K 26/0624; B23K 26/083; B23K 26/24; B23K 2201/34
(Continued)

(56) References Cited

U.S. PATENT DOCUMENTS 4,832,982 A * 5/1989 Mori .................. B23K 26/34
148/903
5,017,753 A * 5/1991 Deckard ............... B29C 64/153
219/121.63
(Continued)

FOREIGN PATENT DOCUMENTS

DE 10252529 B3 8/2004
EP 0622476 A1 11/1994
EP 2578180 A1 4/2013

OTHER PUBLICATIONS

International Search Report and Written Opinion dated Mar. 31, 2015 for counterpart PCT application No. PCT/EP2015/051505.
(Continued)

*Primary Examiner* — Christopher S Kim
(74) *Attorney, Agent, or Firm* — Shuttleworth & Ingersoll, PLC; Timothy J. Klima

(57) ABSTRACT

The invention relates to a method for producing an instrument, in particular a dental instrument or a medical instrument, in which method a blank is produced and is subsequently coated at least partially with abrasive particles, wherein the abrasive particles, in a mixture with carrier particles, are fed onto the surface to be coated and are melted onto the surface by means of a laser.

11 Claims, 3 Drawing Sheets

Figure 1:
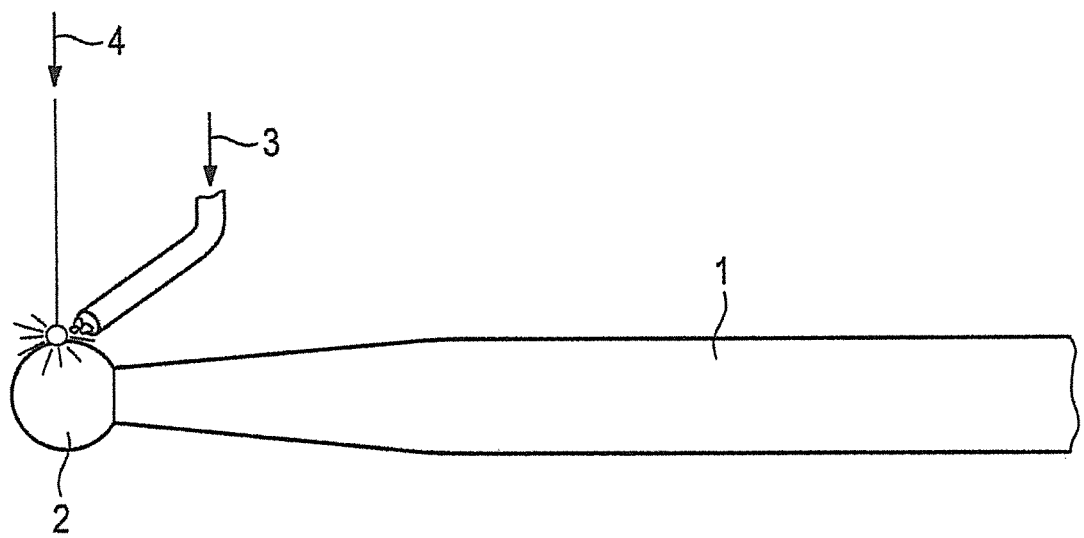

(51) Int. Cl.
  *A61C 3/02*       (2006.01)
  *B23K 26/0622*    (2014.01)
  *B23K 26/70*      (2014.01)
  *B23K 26/00*      (2014.01)
  *B23K 26/08*      (2014.01)
  *B23K 101/34*     (2006.01)
  *B23K 103/04*     (2006.01)
  *B23K 103/14*     (2006.01)
  *B23K 103/16*     (2006.01)
  *B23K 103/00*     (2006.01)
  *A61C 3/06*       (2006.01)
  *B23K 101/04*     (2006.01)
  *B23K 101/20*     (2006.01)
  *B23K 103/18*     (2006.01)

(52) U.S. Cl.
  CPC ........ *B23K 26/0624* (2015.10); *B23K 26/083* (2013.01); *B23K 26/0869* (2013.01); *B23K 26/702* (2015.10); *C23C 24/103* (2013.01); *A61C 3/06* (2013.01); *B23K 2101/04* (2018.08); *B23K 2101/20* (2018.08); *B23K 2101/34* (2018.08); *B23K 2103/04* (2018.08); *B23K 2103/14* (2018.08); *B23K 2103/16* (2018.08); *B23K 2103/18* (2018.08); *B23K 2103/42* (2018.08); *B23K 2103/50* (2018.08); *B23K 2103/52* (2018.08)

(58) Field of Classification Search
  USPC .......................... 219/121.63, 121.64, 121.84
  See application file for complete search history.

(56) References Cited

U.S. PATENT DOCUMENTS

| | | | |
|---|---|---|---|
| 5,740,941 A | * | 4/1998 | Lemelson ............ A47G 19/00 220/62.15 |
| 6,146,476 A | | 11/2000 | Boyer |
| 2013/0089833 A1 | | 4/2013 | Schoen |

OTHER PUBLICATIONS

German Office Action dated Nov. 5, 2014 from counterpart German App No. 10 2014 203 459.0.
German Office Action dated Aug. 12, 2019 from counterpart German Patent Application No. 10 2014 203 459.0.

* cited by examiner

METHOD FOR PRODUCING A DENTAL OR MEDICAL INSTRUMENT

This application is the National Phase of International Application PCT/EP2015/051505 filed Jan. 26, 2016 which designated the U.S.

This application claims priority to German Patent Application 102014203459.0 filed Feb. 26, 2014, the entirety of which is incorporated by reference herein.

The invention relates to a method for producing an instrument, in particular a dental instrument or a medical instrument.

In the prior art there are many different designs of instruments of the abovementioned type in which functional surfaces are coated with abrasive particles. These are usually diamond grains. These are secured galvanically to the surface of the instrument in the prior art.

Galvanic bonding of abrasive particles on dental instruments or medical instruments (the same applies to technical grinding tools, for example for jewelry production or for use in dental laboratories) generally has the disadvantage that the patient comes into contact with the bonding material during the use of the instrument. Particularly if nickel or nickel-containing alloys are used, the patient may suffer undesirable reactions. It was therefore attempted, in the prior art, to make the galvanic bond free of nickel or to cover a coating, which contains nickel, by means of an additional covering layer. These procedures are labor-intensive and are thus associated with high costs. Moreover, there is the disadvantage that the provision of the galvanic baths and the preparation of the baths involve great effort, also in respect of environmental protection. In addition, galvanic baths require time for the galvanic bonding of the abrasive particles. This too is a factor that increases costs.

The object of the invention is to make available a method which is of the type mentioned at the outset and which, while having a simple set-up and being easy to carry out safely, permits reliable coating of a surface of an instrument with abrasive particles.

The object is achieved by a combination of features as disclosed herein, with further advantageous embodiments being set forth in the present disclosure.

Thus, according to the invention, a blank is first of all produced. This blank usually has the desired final dimensions of the instrument, apart from the coating with the abrasive particles, and it requires only to be coated with the abrasive particles. These are applied, for example, on a work head or on functional surfaces, as is known from the prior art. According to the invention, provision is made that the abrasive particles are fixed by means of a laser. For this purpose, a mixture of the abrasive particles with carrier particles is applied to the surface that is to be coated. The carrier particles are melted partially on by means of the laser and in this way fix the abrasive particles.

According to the invention, the blank is preferably produced by means of methods involving material removal, for example turning or milling. The blank, which can also be referred to as a molding, can be produced, for example, from high-strength steel, from titanium, from nickel-titanium alloy, from hard metal, from high-performance plastic such as PEEK, or from ceramic.

In an expedient embodiment of the invention, provision is made that the blank is worked by means of a CNC-controlled machining device in order to apply the abrasive particles. This entails a relative movement on the one hand between the blank and on the other hand between the particle feed and the laser. According to the invention, it is possible for the laser and the particle feed to be left stationary, while the blank is moved relative to these. However, it is also possible the keep the blank stationary and to move the laser and the particle feed. In each case, provision is made that contiguous trajectories of the mixture of abrasive particles and carrier particles are melted on by the laser. According to the invention, it is possible for the coating to be in one layer or several layers. It is also possible for layers of abrasive particles and carrier particles to be applied in different thicknesses or contours to specific areas of the instrument. In this way, it is possible to provide certain areas of the instrument with a thicker coating of abrasive particles and/or to improve the removing behavior of the active surfaces of the instrument by contouring.

According to the invention, the carrier particles are preferably metallic particles or contain metallic particles. For example, the particles can be composed of steel, steel alloys, titanium or titanium alloys or other suitable metals. Biocompatible materials are preferably used. The carrier particles can have identical or different grain sizes.

In the method according to the invention, it is possible to use identical abrasive particles or to provide a mixture of different abrasive particles. Overall, the abrasive particles can be in the form of diamond grains which are natural diamond grains or synthetic diamond grains. It is also possible to use coated grains as abrasive particles. Besides diamond grains, the method according to the invention is also suitable for other abrasive particles or abrasive grains, for example of corundum, silicon carbide or boron nitride or of polycrystalline diamond. As has been mentioned, a mixture of different abrasive particles in terms of their grain sizes and/or their chemical compositions can be used in the method according to the invention.

It is particularly expedient if the grain sizes of the abrasive particles are between 5 µm and 850 µm.

The laser used in the method according to the invention is preferably a short-pulse or ultrashort-pulse laser, for example a femtosecond, picosecond or nanosecond laser.

The method according to the invention can also be modified such that it can be carried out as an additive production method. The mixture of abrasive particles and carrier particles can in this case be applied in layers to the surface to be coated and melted on by means of the laser. Here, the blank is located in a container such that the layered application of the mixture of abrasive particles and carrier particles is possible. This variant of the invention makes it possible in particular to secure thicker layers or multiple layers of abrasive particles on the surface of the blank.

The invention also relates in particular to the use of a laser application method (as described above) for dental instruments or medical instruments.

Figure 2:
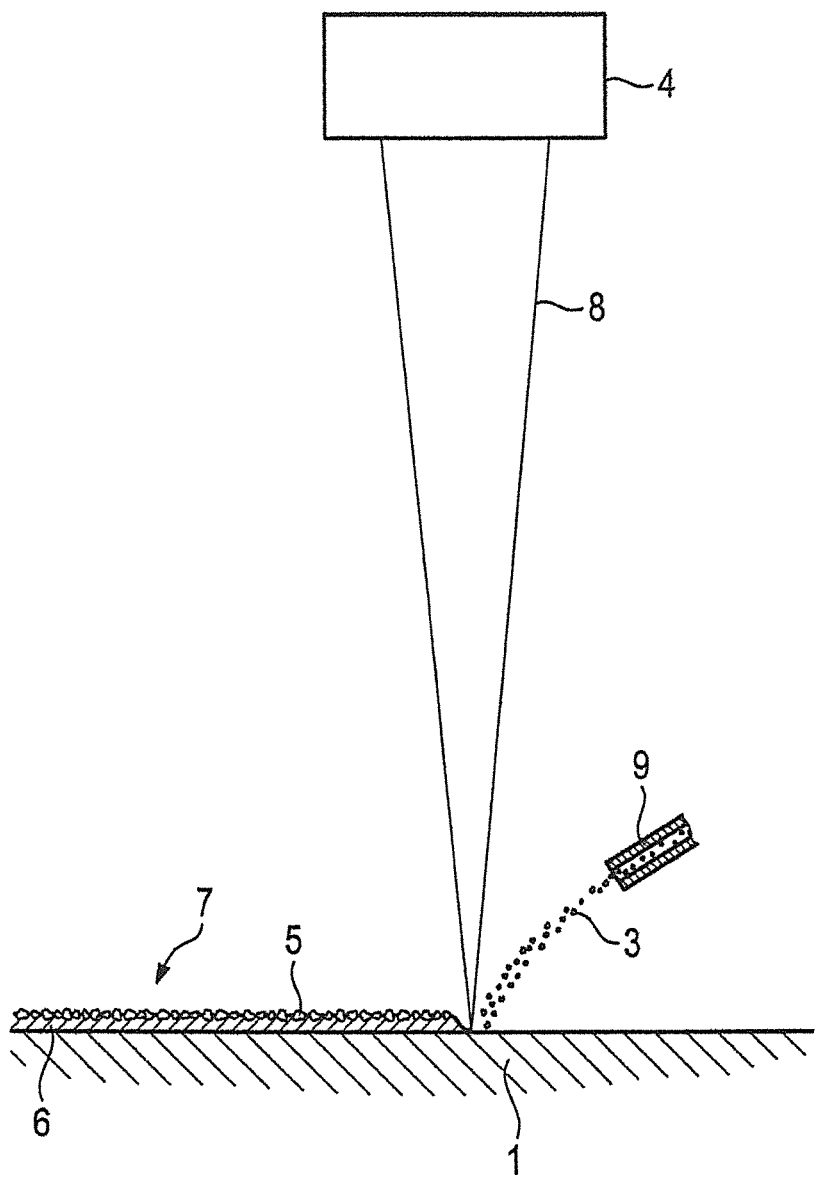
Figure 3:
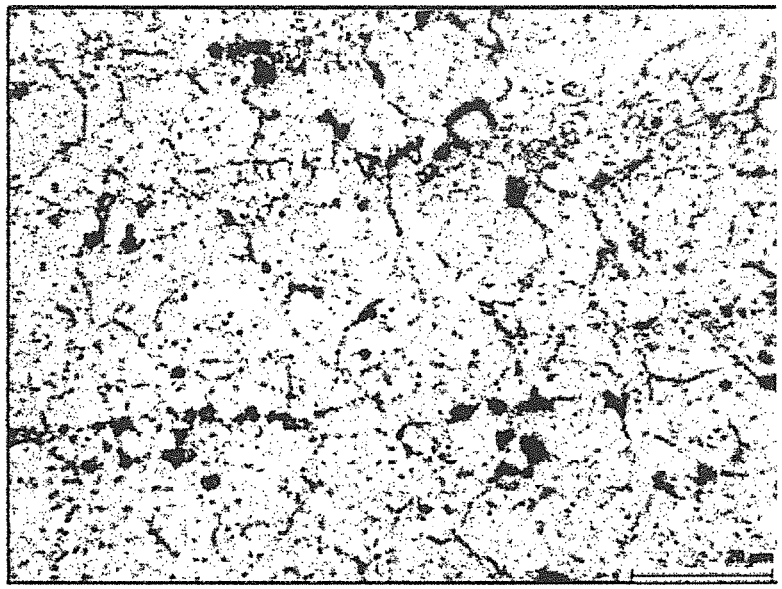
Figure 4:
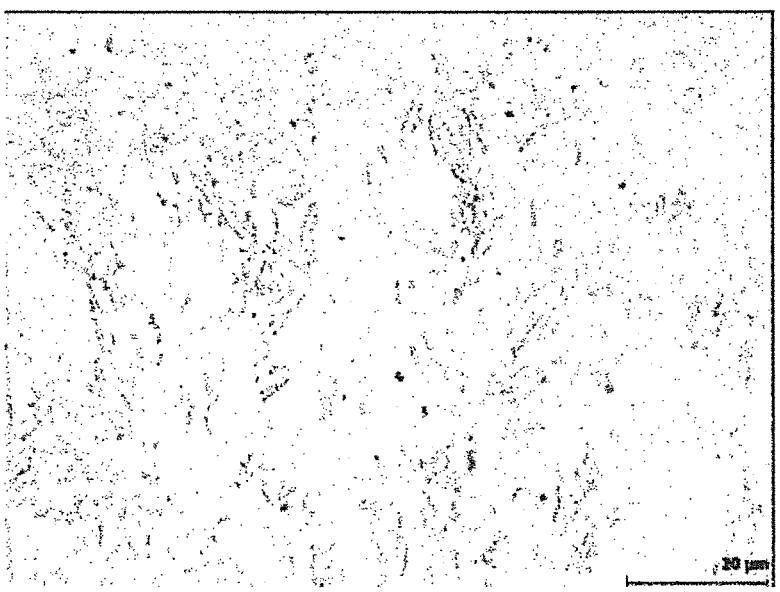

The invention is described below on the basis of an illustrative embodiment and with reference to the drawing, in which:

FIG. 1 shows a schematic view of a blank according to the invention during the coating with abrasive particles with the aid of a laser beam, FIG. 2 shows a schematic and enlarged view of the coating process, FIG. 3 shows a micrograph of the typical structure of drawn steel with subsequent heat treatment, and FIG. 4 shows a micrograph of a material generated by an additive laser fusion method.

FIG. 1 shows a blank 1, of which the contour has been prepared in advance by material removal. The blank 1 comprises a shaft and, secured integrally on the latter, a head 2. The head 2 is coated with abrasive particles by means of the method according to the invention. For this purpose, a feed 3 for a mixture of abrasive particles and carrier particles is provided. This mixture is melted on by means of a laser 4, such that the abrasive particles are securely anchored on the surface of the blank 1.

FIG. 2 shows an enlarged view of the method sequence according to the invention. The surface of the blank 1 is shown in simplified form. A mixture of carrier particles and abrasive particles (feed 3) is applied onto said surface by means of a feed nozzle. At the point of impact of the mixture, a laser beam 8 emerging from the laser 4 impacts the mixture and melts the latter partially on, without melting the abrasive particles and without this damaging the surface of the blank 1. Its material properties are not impaired by the laser (short-pulse or ultrashort-pulse laser) used according to the invention. A coating 7 thus forms which comprises abrasive particles 5 and a carrier layer 6 and forms a surface having a plurality of peaks formed by the protruding abrasive particles; a plurality of depressions formed by the exposed surface of the carrier particles, the plurality of depressions interspersed between the plurality of peaks and having a lower height with respect to the surface of the blank as compared to the plurality of peaks; and a topography between the plurality of peaks and the plurality of depressions, the topography being exposed. The carrier layer 6 is composed of the melted-on carrier particles.

FIGS. 3 and 4 show micrographs allowing a comparison between a conventionally generated material and a material generated by means of an additive method.

The micrograph shown in FIG. 3 is that of a conventionally produced material which has the typical structure of drawn steel with subsequent heat treatment. The carbides arranged lengthwise in the martensitic matrix can be clearly seen.

FIG. 4, by contrast, shows a micrograph of a material generated by means of an additive laser fusion method. The view of the structure clearly shows a coarse, martensitic structure with fine carbide dispersions, which have no particular arrangement. In additively produced workpieces, it proves advantageous that these do not form hardening cracks, as is the case in conventionally generated workpieces.

LIST OF REFERENCE SIGNS 1 blank
2 head
3 delivery of a mixture of carrier particles and abrasive particles
4 laser
5 abrasive particles
6 carrier layer
7 coating
8 laser beam
9 feed nozzle

The invention claimed is:

1. A method for producing a dental instrument or a medical instrument for grinding or polishing, comprising:
   providing a blank,
   subsequently coating the blank at least partially with abrasive particles by including the abrasive particles in a mixture with carrier particles and feeding the mixture onto a surface of the blank to be coated,
   melting the carrier particles onto the surface of the blank to be coated with a laser to fix the abrasive particles such that the abrasive particles are not melted and a portion of the abrasive particles protrudes above an exposed surface of the carrier particles melted onto the surface of the blank to be coated to provide an uneven surface, the uneven surface including:
      a plurality of peaks formed by the protruding abrasive particles;
      a plurality of depressions formed by the exposed surface of the carrier particles, the plurality of depressions interspersed between the plurality of peaks and having a lower height with respect to the surface of the blank as compared to the plurality of peaks;
      a topography between the plurality of peaks and the plurality of depressions, the topography being exposed;
   wherein the abrasive particles continue to have a same physical structure after the melting as when included in the mixture prior to the melting.

2. The method as claimed in claim 1, wherein the coating is performed with a computer numerically controlled machining device to provide a relative movement between the blank and the laser and a particle feed device for feeding the mixture of carrier particles and abrasive particles.

3. The method as claimed in claim 2, wherein the blank is moved relative to the laser and the particle feed device.

4. The method as claimed in claim 2, wherein the laser and the particle feed device are moved relative to the blank.

5. The method as claimed in claim 1, wherein the carrier particles include metallic particles.

6. The method as claimed in claim 5, wherein the carrier particles comprise at least one chosen from steel, titanium and a titanium alloy.

7. The method as claimed in claim 1, wherein the carrier particles have different particle sizes.

8. The method as claimed in claim 1, wherein the laser is at least one chosen from a short-pulse or ultrashort-pulse laser.

9. The method as claimed in claim 8, wherein the laser is at least one chosen from a femtosecond, picosecond and nanosecond laser.

10. The method as claimed in claim 1, wherein the abrasive particles have grain sizes of between 5 µm and 850 µm.

11. The method as claimed in claim 1, wherein the carrier particles have identical particle sizes.

* * * * *